(12) United States Patent
Wollenberg

(10) Patent No.: US 7,380,441 B2
(45) Date of Patent: Jun. 3, 2008

(54) HIGH THROUGHPUT SCREENING METHODS FOR LUBRICATING OIL COMPOSITIONS

(75) Inventor: Robert H. Wollenberg, Orinda, CA (US)

(73) Assignee: Chevron Oronite Company, LLC, San Ramon, CA (US)

( * ) Notice: Subject to any disclaimer, the term of this patent is extended or adjusted under 35 U.S.C. 154(b) by 0 days.

(21) Appl. No.: 11/582,747

(22) Filed: Oct. 18, 2006

(65) Prior Publication Data

US 2007/0039378 A1 Feb. 22, 2007

Related U.S. Application Data

(62) Division of application No. 10/779,424, filed on Feb. 13, 2004, now Pat. No. 7,137,289.

(51) Int. Cl.
*G01N 33/30* (2006.01)
*G01N 33/26* (2006.01)

(52) U.S. Cl. ............. 73/53.05; 73/53.01; 73/61.41

(58) Field of Classification Search ......... 73/53.01, 73/53.05, 60.11, 61.41
See application file for complete search history.

(56) References Cited

U.S. PATENT DOCUMENTS

| | | | |
|---|---|---|---|
| 4,219,432 A | 8/1980 | Girgenti et al. | |
| 4,255,589 A | 3/1981 | Wisotsky | |
| 4,384,138 A | 5/1983 | Karll et al. | 562/478 |
| 4,402,844 A | 9/1983 | Trepka | 508/268 |
| 4,427,834 A | 1/1984 | Martin | 525/280 |
| 5,849,047 A | 12/1998 | Yu et al. | |
| 5,959,297 A | 9/1999 | Weinberg et al. | |
| 5,985,356 A | 11/1999 | Shultz et al. | |
| 6,004,617 A | 12/1999 | Shultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,150,309 A * | 11/2000 | Gao et al. | 508/364 |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,296,771 B1 | 10/2001 | Miroslav | |
| 6,326,090 B1 | 12/2001 | Shultz et al. | |
| 6,336,353 B2 | 1/2002 | Matsiev et al. | |

(Continued)

FOREIGN PATENT DOCUMENTS

WO 02/07870 1/2002

*Primary Examiner*—Daniel S. Larkin
(74) *Attorney, Agent, or Firm*—Claude J. Caroli; M. Carmen & Associates, PLLC

(57) ABSTRACT

Method for determining dispersancy performance for a plurality of fluid samples of different compositions is provided. Each sample includes one or more base oils of lubricating viscosity and one or more lubricating oil additives and a predetermined amount of an oil-insoluble material. The methods can advantageously be optimized using combinatorial chemistry, in which a database of combinations of lubricating oil compositions are generated. As market conditions vary and/or product requirements or customer specifications change, conditions suitable for forming desired products can be identified with little or no downtime.

33 Claims, 2 Drawing Sheets

U.S. PATENT DOCUMENTS

| | | |
|---|---|---|
| 6,345,528 B2 | 2/2002 | Petro et al. |
| 6,346,290 B1 | 2/2002 | Schultz et al. |
| 6,371,640 B1 | 4/2002 | Hajduk et al. |
| 6,373,570 B1 | 4/2002 | McFarland et al. |
| 6,393,895 B1 | 5/2002 | Matsiev et al. |
| 6,393,898 B1 | 5/2002 | Hajduk et al. |
| 6,395,552 B1 | 5/2002 | Borade et al. |
| 6,401,519 B1 | 6/2002 | McFarland et al. |
| 6,406,632 B1 | 6/2002 | Safir et al. |
| 6,410,331 B1 | 6/2002 | Schultz et al. |
| 6,419,881 B1 | 7/2002 | Weinberg et al. |
| 6,420,179 B1 | 7/2002 | Schultz et al. |
| 6,436,292 B1 | 8/2002 | Petro |
| 6,438,497 B1 | 8/2002 | Mansky et al. |
| 6,440,745 B1 | 8/2002 | Weinberg et al. |
| 6,441,901 B2 | 8/2002 | McFarland et al. |
| 6,451,259 B1 | 9/2002 | Cohen et al. |
| 6,461,515 B1 | 10/2002 | Safir et al. |
| 6,468,806 B1 | 10/2002 | McFarland et al. |
| 6,475,391 B2 | 11/2002 | Safir et al. |
| 6,484,567 B1 | 11/2002 | Hajduk et al. |
| 6,491,816 B2 | 12/2002 | Petro |
| 6,508,984 B1 | 1/2003 | Turner et al. |
| 6,519,032 B1 | 2/2003 | Kuebler et al. |
| 6,528,026 B2 | 3/2003 | Hajduk et al. |
| 6,535,284 B1 | 3/2003 | Hajduk et al. |
| 6,535,824 B1 | 3/2003 | Mansky et al. |
| 6,536,944 B1 | 3/2003 | Archibald et al. |
| 6,541,271 B1 | 4/2003 | McFarland et al. |
| 6,553,318 B2 | 4/2003 | Mansky |
| 6,576,906 B1 | 6/2003 | Archibald et al. |
| 6,577,392 B1 | 6/2003 | Nielsen et al. |
| 6,582,116 B2 | 6/2003 | Nielsen |
| 6,605,473 B1 | 8/2003 | Hajduk et al. |
| 6,644,101 B2 | 11/2003 | Hajduk et al. |
| 6,649,413 B1 | 11/2003 | Schultz et al. |
| 6,650,102 B2 | 11/2003 | Hajduk et al. |
| 6,653,138 B1 | 11/2003 | Turner et al. |
| 6,655,194 B2 | 12/2003 | Hajduk et al. |
| 6,658,429 B2 | 12/2003 | Dorsett, Jr. |
| 6,664,067 B1 | 12/2003 | Hajduk et al. |
| 6,668,622 B2 | 12/2003 | Hajduk et al. |
| 6,670,298 B1 | 12/2003 | Weinberg et al. |
| 6,679,130 B2 | 1/2004 | Hajduk et al. |
| 6,681,618 B2 | 1/2004 | Hajduk et al. |
| 6,686,205 B1 | 2/2004 | Schultz et al. |
| 6,690,179 B2 | 2/2004 | Hajduk et al. |
| 2002/0023507 A1 | 2/2002 | Hajduk et al. |
| 2002/0028456 A1 | 3/2002 | Mansky et al. |
| 2002/0029621 A1 | 3/2002 | Hajduk et al. |
| 2002/0032531 A1 | 3/2002 | Mansky et al. |
| 2002/0098332 A1 | 7/2002 | Warren et al. |
| 2002/0148282 A1 | 10/2002 | Hajduk et al. |
| 2002/0155036 A1 | 10/2002 | Hajduk et al. |
| 2002/0164275 A1 | 11/2002 | Wheeler et al. |
| 2003/0007152 A1 | 1/2003 | McFarland et al. |
| 2003/0032198 A1 | 2/2003 | Lugmair et al. |
| 2003/0032205 A1 | 2/2003 | McFarland et al. |
| 2003/0037601 A1 | 2/2003 | Mansky et al. |
| 2003/0037620 A1 | 2/2003 | Mansky |
| 2003/0041653 A1 | 3/2003 | Matsiev et al. |
| 2003/0041671 A1 | 3/2003 | Hajduk et al. |
| 2003/0041672 A1 | 3/2003 | Hajduk et al. |
| 2003/0041676 A1 | 3/2003 | Hajduk et al. |
| 2003/0054740 A1 | 3/2003 | Mansky |
| 2003/0055587 A1 | 3/2003 | Wang et al. |
| 2003/0056576 A1 | 3/2003 | Mansky |
| 2003/0068829 A1 | 4/2003 | Giaquinta et al. |
| 2003/0097871 A1 | 5/2003 | Mansky |
| 2003/0100119 A1 | 5/2003 | Weinberg et al. |
| 2003/0127776 A1 | 7/2003 | Carlson et al. |
| 2003/0133113 A1 | 7/2003 | Hajduk et al. |
| 2003/0138025 A1 | 7/2003 | Archibald et al. |
| 2003/0141613 A1 | 7/2003 | Hajduk et al. |
| 2003/0142309 A1 | 7/2003 | Kuebler et al. |
| 2003/0157721 A1 | 8/2003 | Turner et al. |
| 2003/0161763 A1 | 8/2003 | Erden et al. |
| 2003/0169638 A1 | 9/2003 | Nielsen |
| 2003/0190260 A1 | 10/2003 | Wheeler et al. |
| 2003/0203500 A1 | 10/2003 | Carlson et al. |
| 2003/0211016 A1 | 11/2003 | Dales et al. |
| 2003/0218467 A1 | 11/2003 | Carlson et al. |
| 2003/0219906 A1 | 11/2003 | Giaquinta et al. |
| 2004/0123650 A1 | 7/2004 | Kolosov et al. |

\* cited by examiner

HIGH THROUGHPUT SCREENING METHODS FOR LUBRICATING OIL COMPOSITIONS

This application is a divisional of U.S. patent application Ser. No. 10/779,424, filed Feb. 13, 2004, now U.S. Pat. No. 7,137,289, the contents of which are incorporated herein by reference.

BACKGROUND OF THE INVENTION

1. Technical Field

The present invention relates generally to high throughput screening of lubricating oil compositions for lubricant performance.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by June 2004 and below 0.05 wt. % by January 2006. Also, at present, there is no industry standard requirement for sulfur content in engine oils, but it has been proposed that the sulfur content be below 0.3 wt. % to meet June 2007 requirements for emissions. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions for information correlating to the actual useful properties of the compositions.

For example, it would be desirable to evaluate multiple lubricating oil compositions for dispersancy. Dispersants are added to lubricating oil compositions to keep engines clean by dispersing sludge, soot and varnish-forming deposits in the oil. Sludge can form in an internal combustion engine when, for example, combustion products such as, for example, water, metal particles produced by engine wear, and various partially oxidized hydrocarbon molecules, enter the lubricating oil by blowing past the piston rings. The sludge is a highly viscous composition which inhibits proper flow of the lubricating oil, thereby impairing its effectiveness. The problem can be partially alleviated by running an engine hot over an extended period of time by, for example, extended highway driving, to evaporate the water component of the sludge and loosen up the oil. This allows the filter to work more effectively to remove abrasive particulates which contribute to engine wear. However, with stop-and-go traffic or short trips in city driving, sludge has a tendency to build up. Hence, the importance of identifying and selecting the most effective additives to prevent such a build up. Dispersants also keep soot particles small by preventing agglomeration.

Another consideration is how the various additives in the lubricating oil interact. The presence of one additive may affect the performance of another. Accordingly, testing for any particular performance property is complicated by the fact that an additive cannot be tested in isolation. Rather, many different lubricating oil formulations with various additives and percentage compositions must be tested.

Accordingly, it would be desirable to rapidly prepare and test for dispersancy a plurality of sample candidate lubricating oil compositions automatically, preferably utilizing small amounts of each sample.

SUMMARY OF THE INVENTION

A high throughput screening method for determining lubricant performance is provided herein. In accordance with one embodiment of the present invention, a high throughput method for screening lubricating oil composition samples for dispersancy performance, under program control, is provided comprising the steps of (a) providing a plurality of different lubricating oil composition samples, each sample comprising (i) a major amount of at least one base oil of lubricating viscosity, (ii) a minor amount of at least one lubricating oil additive and (iii) a predetermined amount of a base oil-insoluble material; (b) measuring the dispersancy performance of each sample to provide corresponding dispersancy performance data results; and, (c) outputting the results of step (b).

In a second embodiment of the present invention, a system for screening lubricant performance, under program control, is provided comprising (a) a plurality of test receptacles, each receptacle containing a different lubricating oil composition sample comprising (i) a major amount of at least one base oil of lubricating viscosity, (ii) a minor amount of at least one lubricating oil additive and (iii) a predetermined amount of a base oil-insoluble material; (b) receptacle moving means for individually positioning the test receptacles in a testing station for measurement of dispersancy performance of the respective sample; and (c) means for measuring the dispersancy performance of the sample in the testing station to obtain dispersancy performance data associated with the sample and for transferring the dispersancy performance data to a computer controller.

The methods and systems of the present invention advantageously permit the screening of many different composition samples in an efficient manner to determine optimal dispersancy characteristics of the samples.

BRIEF DESCRIPTION OF THE DRAWINGS

Various embodiments are described below with reference to the drawings wherein.

DETAILED DESCRIPTION OF THE PREFERRED EMBODIMENT(S)

Figure 1:
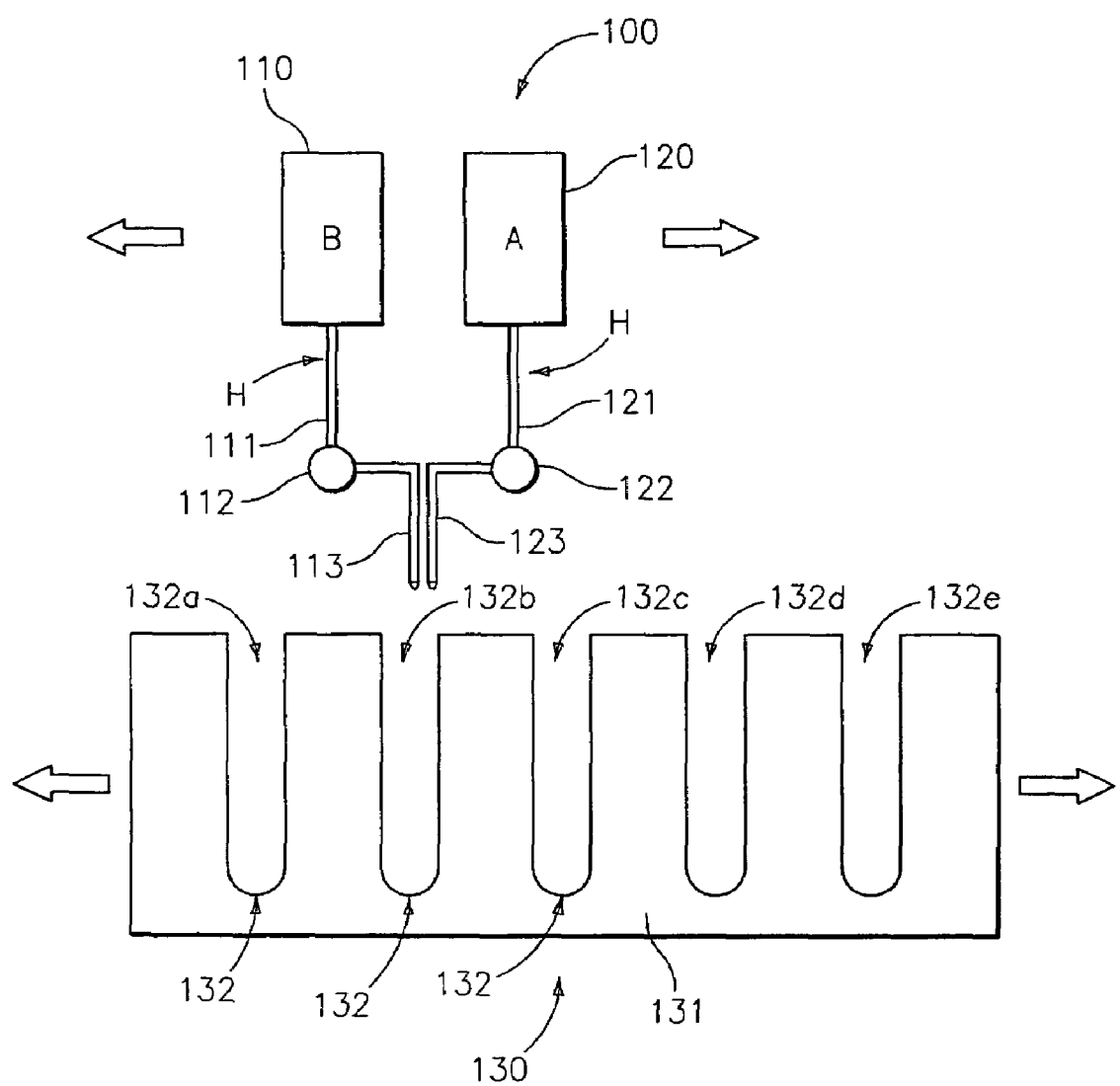
FIG. 1 is a schematic diagram of a system for preparing a plurality of different lubricating oil compositions; and, FIG. 2 is a schematic illustration of a dispensing system of the invention.

The present invention is directed to a method for the high throughput screening of a plurality of different lubricating oil compositions containing lubricating oil compositions for lubricant performance properties, e.g., dispersancy performance. The expression "high throughput" as used herein shall be understood to mean that a relatively large number of different lubricating oil compositions can be rapidly prepared and analyzed. In a first step of one embodiment of the screening method of the present invention, at least one lubricating oil composition is introduced in a plurality of respective test receptacles so that each receptacle contains a different lubricating oil composition having a different composition depending upon the percentage amounts and/or types of the at least one base oil and/or at least one additive combined in each receptacle.

Data regarding the composition of each sample are stored in a data library. Adding the information related to the dispersancy data of each of the stored compositions substantially facilitates the selection of candidate compositions capable of successfully carrying out the dispersancy tests under the desired operating conditions or statutory requirements. Accordingly, storing this information in the combinatorial library not only allows for a rapid selection of multiple lubricating oil compositions in response to new requirements for a given test, but also becomes another piece of information in addition to, for example, storage stability, oxidation stability, wear stability, deposit formation data, elastomer compatibility, etc., of the cataloged compositions. This information may also allow for calculating necessary changes of the additives at the least cost. The procedure is advantageously accomplished under program control and automatically controlled by, for example, a microprocessor or other computer control device. The expression "program control" as used herein shall be understood to mean the equipment used herein in providing the plurality of lubricating oil compositions is automated and controlled by a microprocessor or other computer control device.

The lubricating oil compositions for use in the high throughput screening method of this invention include at least one base oil of lubricating viscosity and at least one lubricating oil additive. Generally, the lubricating oil compositions for use in the high throughput screening method of this invention include a minor amount of at least one lubricating oil additive together with a major amount of at least one base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition.

The expression "base oil" as used herein shall be understood to mean a base stock or blend of base stocks which is a lubricant component that is produced by a single manufacturer to the same specifications (independent of feed source or manufacturer's location): that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, natural gas engine oils, railroad oils, two-cycle engine oils, tractor oils, heavy duty diesel engine oils, truck oils and functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, -5W-20, 5W-30, 5W-40, 5W-50, 5W-60, 10W, 10W-20, 10W-30, 10W40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the lubricating oil compositions herein is at least one lubricating oil additive. The lubricating oil additives for use herein can be any presently known or later-discovered additive used in formulating lubricating oil compositions. Suitable lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein. Preferably, the at least one lubricating oil additive is a dispersant.

If desired, the lubricating oil additive(s) can further contain a diluent oil to form an additive concentrate. These concentrates usually include at least from about 98 wt. % to about 10 wt. %, preferably from about 98 wt. % to about 25 wt. % and most preferably from about 97 wt. % to about 50 wt. % of a diluent oil and from about 2 wt. % to about 90 wt. %, preferably from about 2 wt. % to about 75 wt. % and most preferably from about 3 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; sulfur-containing materials, e.g., sulfurized olefins or esters and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonamides, thiophosphonamides and phosphoramides; thiazoles, e.g., 2,5-dimercapto-1,3,4-thiadiazoles, mercaptobenzothiazoles and derivatives thereof, triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof.

The polyalkylene succinic anhydride dispersant is preferably a polyisobutenyl succinic anhydride (PIBSA). The number average molecular weight of the polyalkylene tail in the polyalkylene succinic anhydrides used herein will be at least 350, preferably from about to about 750 to about 3000 and most preferably from about 900 to about 1100. Examples of suitable polyalkylene succinic anhydrides for use herein are thermal PIBSA (polyisobutenyl succinic anhydride) described in U.S. Pat. No. 3,361,673; chlorinated PIBSA described in U.S. Pat. No. 3,172,892; a mixture of thermal and chlorinated PIBSA described in U.S. Pat. No. 3,912,764; high succinic ratio PIBSA described in U.S. Pat. No. 4,234,435; polyPIBSA described in U.S. Pat. Nos. 5,112,507 and 5,175,225; high succinic ratio polyPIBSA described in U.S. Pat. Nos. 5,565,528 and 5,616,668; free radical PIBSA described in U.S. Pat. Nos. 5,286,799, 5,319,030 and 5,625,004; PIBSA made from high methylvinylidene polybutene described in U.S. Pat. Nos. 4,152,499, 5,137,978 and 5,137,980; high succinic ratio PIBSA made from high methylvinylidene polybutene described in European Patent Application Publication No. EP 355 895; terpolymer PIBSA described in U.S. Pat. No. 5,792,729, sulfonic acid PIBSA described in U.S. Pat. No. 5,777,025. and European Patent Application Publication No. EP 542 380; and purified PIBSA described in U.S. Pat. No. 5,523,417 and European Patent Application Publication No. EP 602 863, the contents of each of these references being incorporated herein by reference.

Non-nitrogen containing derivatives of polyalkylene succinic anhydrides include, but are not limited to, succinic acids, Group I and/or Group II mono- or di-metal salts of succinic acids, succinate esters formed by the reaction of a polyalkylene succinic anhydride, acid chloride, or other derivatives with an alcohol (e.g., HOR$^1$ wherein R$^1$ is an alkyl group of from 1 to 10 carbon atoms) and the like and mixtures thereof.

If desired, the foregoing polyalkylene succinic anhydrides and/or non-nitrogen-containing derivatives thereof can be post-treated with a wide variety of post-treating reagents. For example, the foregoing polyalkylene succinic anhydride and/or derivatives thereof can be reacted with boron or a cyclic carbonate, e.g., ethylene carbonate, to provide borate post-treated and ethylene carbonate post-treated products.

The basic nitrogen compound for use herein must contain basic nitrogen as measured, for example, by ASTM D664 test or D2896. The basic nitrogen compounds are selected from the group consisting of succinimides, polysuccinimides, carboxylic acid amides, hydrocarbyl monoamines, hydrocarbon polyamines, Mannich bases, phosphoramides, thiophosphoramides, phosphonamides, dispersant viscosity index improvers, and mixtures thereof. These basic nitrogen-containing compounds are described below (keeping in mind the reservation that each must have at least one basic nitrogen). Any of the nitrogen-containing compositions may be post-treated with, e.g., boron or ethylene carbonate, using procedures well known in the art so long as the compositions continue to contain basic nitrogen.

The succinimides and polysuccinimides that can be used herein are disclosed in numerous references and are well known in the art. Certain fundamental types of succinimides and the related materials encompassed by the term of art "succinimide" are taught in U.S. Pat. Nos. 3,219,666; 3,172,892; and 3,272,746, the contents of which are incorporated by reference herein. The term "succinimide" is understood in the art to include many of the amide, imide, and amidine species which may also be formed. The predominant product, however, is a succinimide and this term has been generally accepted as meaning the product of a reaction of an alkenyl substituted succinic acid or anhydride with a nitrogen-containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetramine, tetraethylene pentamine, and higher molecular weight polyethylene amines. Particularly preferred are those succinimides prepared from polyisobutenyl succinic anhydride of 70 to 128 carbon atoms and tetraethylene pentamine or higher molecular weight polyethylene amines or mixtures of polyethylene amines such that the average molecular weight of the mixture is about 205 Daltons.

Also included within the term "succinimide" are the co-oligomers of a hydrocarbyl succinic acid or anhydride and a polysecondary amine containing at least one tertiary amino nitrogen in addition to two or more secondary amino groups. Ordinarily, this composition has between 1,500 and 50,000 average molecular weight. A typical compound would be that prepared by reacting polyisobutenyl succinic anhydride and ethylene dipiperazine.

Carboxylic acid amide compounds are also useful nitrogen-containing compounds for preparing the colloidal suspensions of this invention. Typical of such compounds are those disclosed in U.S. Pat. No. 3,405,064, the contents of which are incorporated by reference herein. These compounds are ordinarily prepared by reacting a carboxylic acid or anhydride or ester thereof, having at least 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula R$^2$COOH, where R$^2$ is C$_{12-20}$ alkyl or a mixture of this acid with a polyisobutenyl carboxylic acid in which the polyisobutenyl group contains from about 72 to about 128 carbon atoms and (2) an ethylene amine, especially triethylene tetramine or tetraethylene pentamine or mixtures thereof.

Another class of useful nitrogen-containing compounds are hydrocarbyl monoamines and hydrocarbyl polyamines, e.g., those disclosed in U.S. Pat. No. 3,574,576, the contents of which are incorporated by reference herein. The hydrocarbyl group, which is preferably alkyl, or olefinic having one or two sites of unsaturation, usually contains from 9 to about 350 carbon atoms and preferably from about 20 to about 200 carbon atoms. Particularly preferred hydrocarbyl polyamines are those which are derived, e.g., by reacting polyisobutenyl chloride and a polyalkylene polyamine, such as an ethylene amine, e.g., ethylene diamine, diethylene triamine, tetraethylene pentamine, 2-aminoethylpiperazine, 1,3-propylene diamine, 1,2-propylenediamine, and the like.

Yet another class of useful nitrogen-containing compounds are the Mannich base compounds. These compounds are prepared from a phenol or C$_{9-200}$ alkylphenol, an aldehyde, such as formaldehyde or formaldehyde precursor such as paraformaldehyde, and an amine compound. The amine may be a mono or polyamine and typical compounds are prepared from an alkylamine, such as methylamine or an ethylene amine, such as, diethylene triamine, or tetraethylene pentamine, and the like. The phenolic material may be sulfurized and preferably is dodecylphenol or a C$_{80-100}$ alkylphenol. Typical Mannich bases which can be used in this invention are disclosed in U.S. Pat. Nos. 3,539,663, 3,649,229; 3,368,972 and 4,157,309, the contents of which are incorporated by reference herein.

Still yet another class of useful nitrogen-containing compounds are the phosphoramides and phosphonamides such as, for example, those disclosed in U.S. Pat. Nos. 3,909,430 and 3,968,157, the contents of which are incorporated by reference herein. These compounds may be prepared by forming a phosphorus compound having at least one P—N bond. They can be prepared, for example, by reacting phosphorus oxychloride with a hydrocarbyl diol in the presence of a monoamine or by reacting phosphorus oxychloride with a difunctional secondary amine and a monofunctional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and a nitrogen-containing compound as defined above, particularly an alkylamine, alkyldiamine, alkylpolyamine, or an alkyleneimine, such as ethylene diamine, diethylenetriamine, triethylenetetramine, tetraethylenepentamine, and the like.

Another class of useful nitrogen-containing compounds includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. Accordingly, the proposed compounds can be screened to determine, for example, which compounds may perform poorly in an oxidation inhibition process due to a poor ability to trap intermediate peroxides. This can be carried out using known software such as, for example, Quantum Mechanics™ available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compounds libraries with increased probability for finding desirable compounds. For example, the compounds analyzed can be formulated into various lubricating oil compositions, as described hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 10/699,510, filed on Oct. 31, 2003 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. It is to be understood that the present invention is not limited to this system and that other systems can be envisioned for providing the foregoing compositions in the plurality of respective test receptacles.

Generally, vessel 110 contains a supply of the foregoing base oils of lubricating viscosity B. Vessel 120 contains a supply of additive A, which can be any of the foregoing additives useful for modifying the properties of the base oil so as to provide a lubricating oil composition suitable for the intended use or application. As one skilled in the art would readily appreciate, one or more of vessels 110 and vessels 120 can be used when dispensing more than one base oil and one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating lubricating oil additive A to nozzle portion 123, from which it can be dispensed into a selected test reservoir, as described below. The amount of base oil dispensed is determined by metering pump 122, which also can be computer controlled. Computer programs and systems for automatically metering predetermined amounts of materials in accordance with a preselected program control are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of inert material (e.g., glass, ceramic, metal) having a plurality of recesses 132 for receiving the dispensed base oil and additives. The recesses provide test reservoirs wherein each reservoir contains a lubricating oil of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. While five reservoirs, i.e., recesses 132a, 132b, 132c, 132d, 132e, are illustrated in FIG. 1, any number of reservoirs can be employed. For example, a 10×10 array of reservoirs would accommodate 100 different lubricating oil formulation samples. It is also contemplated that liners (not shown), e.g., glass or metal such as aluminum, can be inserted into recesses 132a, 132b, 132c, 132d, 132e prior to depositing the lubricating oil components.

The individual reservoirs are adapted to hold relatively small amounts of lubricating oil samples. The sample size in each reservoir can generally be less than about 50 ml, preferably no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132a. A metered amount of base oil B and a metered amount of additive A are simultaneously dispensed into recess 132a. The dispensing nozzles 113 and 123 are thereafter repositioned to be in alignment with the next recess 132b and the metered amounts of additive A and/or base oil B are changed in accordance with a predetermined schedule of variation such that the lubricating oil in recess 132b has a different percentage composition of additive than that in recess 132a. The pattern is repeated as the nozzles 113 and 123 are sequentially aligned with the successive recesses 132c, 132d, and 132e so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) or by bubbling the reservoir with a gas, e.g., nitrogen.

Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Figure 2:
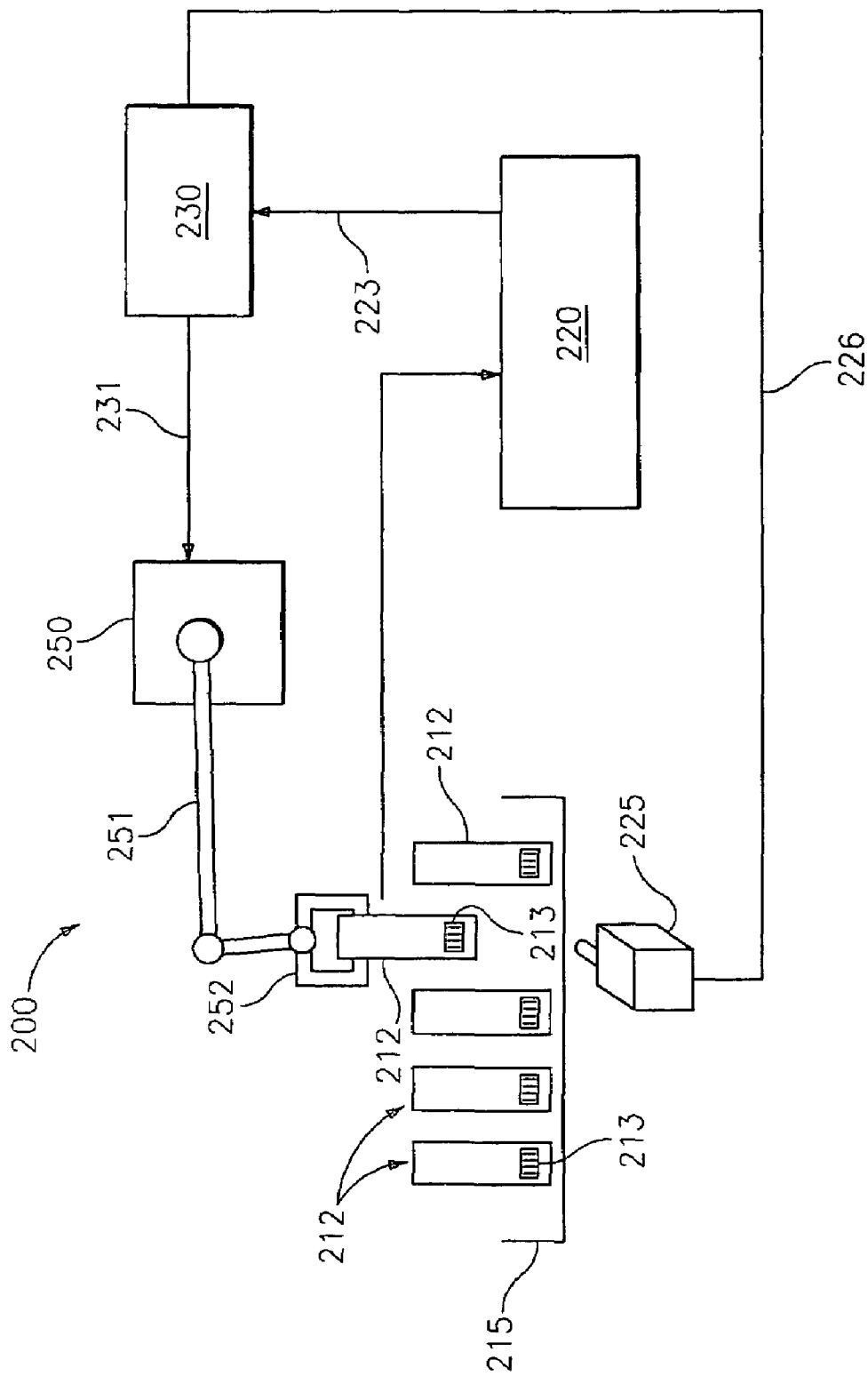

Referring now to FIG. 2, a system 200 for combining and dispensing a lubricating oil composition is schematically illustrated which employs a single nozzle assembly 210 having an elongated injector portion 211 and a mixing chamber 212. The end of injector portion 211 includes an opening 216 through which the lubricating oil composition is ejected into the selected test reservoir.

A conduit 202 conveys a quantity of base oil B through a metering apparatus 201 and into mixing chamber 212. Conduit 204 carries a first additive A-1 through metering apparatus 203 and into mixing chamber 212. Conduit 206 carries a second additive A-2 through metering apparatus 205 and into mixing chamber 212. While only two additive components A-1 and A-2 are shown, it should be understood that any number of different additives can be individually metered into the nozzle assembly 210. The metering apparatus 201, 203, and 205 are each automatically controlled by control system 250 which preferably includes a microprocessor with the appropriate programming and control connections 251, 252 and 253 for communicating control signals to the respective metering apparatus. Control connections 251, 252 and 253 can be, for example, electrical, optical, pneumatic, or fluidic. The control system 250 determines the composition of the lubricating oil in the mixing chamber 212 by regulating the amounts of the respective lubrication oil components (i.e., base oil B, and additives A-1, A-2, etc.) metered into the nozzle assembly 210.

Preferably the conduits 202, 204, and 206 are terminated with one way valves 207, 208, and 209, respectively, to prevent backflow of the mixing chamber contents in the event that pressure in the mixing chamber 212 exceeds the pressure in the conduits.

The lubricating oil components can be mixed together by various means. For example, mixing unit 213 can be a rotary impeller, or, more preferably, an ultrasonic probe. Optionally, baffles 215 can be incorporated into nozzle assembly 210 for static mixing of the components as they flow through the nozzle assembly.

In the event that high viscosity components are being mixed, a heating unit such as coiled resistance heater 218 can be used to raise the temperature of the components and thereby lower their viscosity to improve fluid flow. Heating units can alternatively be convection units (e.g., hot air blowers), radiant coils, or conduction heaters, and can be used to heat any part of the system 200 including the component supplies (B, A-1, A-2), the conduits (202, 204, 206), the metering apparatus (201, 203, 205), the mixing chamber 212, and/or the injector portion 211 (as shown)

The contents of the mixing chamber 212 can be moved through injector portion 211 by, for example, applying pressure from a pressure source P such as compressed gas. As mentioned above, one-way valves 207, 208, and 209 prevent backflow of the contents into the conduits 202, 204, and 206 if the pressure within the mixing chamber 212 exceeds the pressure within the conduits. Alternatively, the base oil and additive sources B, A-1 and A-2 can be pressurized and/or the metering apparatus 201, 203 and 205 can provide pumping pressure to move the materials through the system.

Once the plurality of receptacles have been provided containing lubricating oil compositions, the plurality of fluid samples can then be analyzed for dispersancy performance. The method of the present invention includes testing a plurality of lubricating oil composition samples for dispersancy performance by any of a variety of methods. Typically, the lubricating oil composition is combined with an oil insoluble material, treated by heating to a predetermined temperature for a predetermined period of time, and then tested for an indicator of dispersancy performance, such as, for example, viscosity or spot spreading.

The base oil-insoluble material for use herein can be any polar, base oil-insoluble material. Useful polar, base oil-insoluble material includes, by way of example and with no limitation, sludge deposits, e.g., recovered used engine oil, natural soot, e.g., recovered used engine soot; synthetic soot, e.g., carbon black(s); varnish-forming material; water and the like. Generally, carbon black for use as synthetic soot herein includes any of the commonly available, commercially-produced carbon blacks known to one skilled in the art. Useful carbon blacks include, but are not limited to, furnace black, e.g., super abrasion furnace (SAF) blacks, high abrasion furnace (HAF) blacks, fast extrusion furnace (FEF) blacks, fine furnace (FF) blacks, intermediate super abrasion furnace (ISAF) blacks and semi-reinforcing furnace (SRF) blacks, medium processing channel blacks, hard processing channel blacks, conducting channel blacks, channel blacks, lamp blacks, acetylene blacks, thermal blacks and the like and mixtures thereof. General values for surface areas of usable carbon blacks are set forth below:

| Carbon Blacks | |
| --- | --- |
| ASTM Designation (D-1765-82a) | Surface Area ($m^2/g$) (D-3765) |
| N-110 | 126 |
| N-234 | 120 |
| N-220 | 111 |
| N-339 | 95 |
| N-330 | 83 |
| N-550 | 42 |
| N-660 | 35 |

In one embodiment of the screening method of the present invention, a soot thickening test is performed in which at lest one base oil of lubricating viscosity is combined with at lest one lubricating oil additive (preferably, at least one dispersant additive) in a predetermined amount and composition percentage to provide a lubricating oil composition. A portion of the lubricating oil composition is reserved for use as a comparison sample of fresh lubricant oil composition. The kinematic viscosity of the fresh comparison sample is measured at 100° C. by any suitable method.

To provide a comparative test sample, another portion of the lubricating oil composition is combined with a predetermined amount of a base oil-insoluble material, for example, a synthetic soot such as carbon black, to simulate soot. A predetermined amount of the base oil-insoluble material in the test sample will ordinarily range from about 0.5 to about 10% by weight and preferably from about 1 to about 6% by weight, based on the total weight of the lubricating oil composition.

The base oil-insoluble material is soaked in the lubricating oil composition for a predetermined time period, e.g., a time period ranging from about 10 hours to about 20 hours, after which the sample is homogenized for a time period ranging from about 30 seconds to about 3 minutes. Homogenization can be accomplished by, for example, mechanical stirring or by ultrasonic agitation. The test sample is then degassed in an oven for about 15 minutes to about 1 hour after which the kinematic viscosity of the test sample is measured. The kinematic viscosity of the test sample is then compared with the kinematic viscosity of the fresh lubricating oil comparison sample to determine the percentage increase in viscosity. The more effective the dispersancy performance of the test sample, the smaller will be the increase in viscosity as compared with the fresh sample, because of the dispersancy of the polar, base oil-insoluble material. The dispersancy performance results are then automatically outputted to a computer controller.

In another embodiment of the present invention, a spot dispersion test is performed in which, for example, a test sample is divided into two portions, each containing, for example, about 20 parts by weight of a particular lubricating oil composition combined with about 5 parts by weight of a base oil-insoluble material such as, for example, used engine sludge containing about 2% by weight of carbonaceous material. To one portion, a predetermined amount of distilled water (e.g., about 0.25 parts) is added. Both portions are then homogenized. Multiple spots, e.g., six spots (three spots of each portion) can then be made on respective pieces of a chromatographic material, e.g., filter paper, and treated under the certain conditions such as, e.g., those set forth below:

| Without Water | With Water |
|---|---|
| Spot 1—Room temperature | Spot 4—Room temperature |
| Spot 2—held at about 200° C. for about 10 minutes | Spot 5—held at about 200° C. for about 1 minute |
| Spot 3—held at about 250° C. for about 10 minutes | Spot 6—held at about 200° C. for about 10 minutes |

The spots are then permitted to elute into concentric rings for a predetermined period of time, e.g., up to about 48 hours, and rated by measuring the sludge diameter ($D_S$) and clear oil diameter ($D_O$) of each spot and calculating the ratio of the diameters $D_S/D_O$, i.e., measuring an outer diameter of each ring and an inner diameter of each ring, calculating a ratio of inner diameter to outer diameter for the rings and calculating dispersancy performance data based upon the ratios for the rings. The total of the ratio of all six spots is an indicator of the dispersancy performance of the lubricating oil composition test sample. The better the dispersancy performance of the lubricant oil composition is, the farther the sludge will travel, and the higher will be the ratio $D_S/D_O$, up to a maximum ratio of 1. Such ratios can be derived by, for example, light transmittance determination through the filter paper employing known light transmittance determination equipment.

If desired, the results of the method of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control, commands, may be transmitted, are known.

Dispersancy data regarding each of the compositions described herein can be stored in a relational database to provide a combinatorial lubricating oil composition library. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the lubricating oil compositions and the analytical dispersancy data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of each of the additives and compositions described herein and correlate that information with the information obtained from the dispersancy measurements can be used. This type of software is well known to those of skill in the art.

While the above description contains many specifics, these specifics should not be construed as limitations of the invention, but merely as exemplifications of preferred embodiments thereof. For example, dispersancy tests other than those described herein can be used to provide dispersancy data for the plurality of different samples tested. Those skilled in the art will envision many other embodiments within the scope and spirit of the invention as defined by the claims appended hereto.

What is claimed is:

1. A method for screening lubricating oil composition samples for dispersancy performance, under program control, comprising:
    (a) providing a plurality of different lubricating oil composition samples, each sample comprising: (i) a major amount of at least one base oil of lubricating viscosity,
    (ii) a minor amount of at least one lubricating oil additive, and (iii) a predetermined amount of a base oil-insoluble material selected from the group consisting of natural soot, synthetic soot, varnish-forming material, water and mixtures thereof;

(b) measuring the dispersancy performance of each test sample to provide corresponding dispersancy performance data results; and (c) automatically outputting the results of step (b), which comprises converting the dispersancy performance data of step (b) into a digital signal and sending the digital signal to a microprocessor.

2. The method of claim 1, wherein the base oil is a natural or synthetic oil.

3. The method of claim 1, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents, and mixtures thereof.

4. The method of claim 3, wherein the dispersant is selected from the group consisting of polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonamides, thiophosphonamides and phosphoramides, thiazoles, triazoles, copolymers which contain a carboxylate ester with one or more additional polar function, borate post-treated succinimides, ethylene carbonate post-treated succinimides and mixtures thereof.

5. The method of claim 1, wherein the at least one lubricating oil additive is an ashless dispersant.

6. The method of claim 1, wherein the step of measuring the dispersancy performance of each sample comprises measuring the kinematic viscosity of each sample at a predetermined temperature.

7. The method of claim 6, further comprising:

providing corresponding lubricating oil composition reference samples containing no base oil-insoluble material;

measuring the kinematic viscosity of the corresponding reference samples; and determining the percentage difference between the kinematic viscosity of the lubricating oil composition sample and the corresponding lubricating oil composition reference sample.

8. The method of claim 1, wherein the synthetic soot is carbon black.

9. The method of claim 1, wherein the step of measuring the dispersancy performance of each sample comprises applying to a respective piece of a chromatographic material at least one spot of each sample, permitting the spot to elute into concentric rings, measuring an outer diameter of each ring and an inner diameter of each ring, calculating a ratio of inner diameter to outer diameter for the rings and calculating dispersancy performance data based upon the ratios for the rings.

10. The method of claim 9, wherein the step of measuring the outer diameter of each ring and the inner diameter of each ring comprises transmitting a light through light and dark areas of the chromatographic material.

11. The method of claim 9, wherein the chromatographic material is filter paper.

12. The method of claim 1, wherein the lubricating oil composition samples have a volume of no more than about 50 ml.

13. The method of claim 1, wherein the lubricating oil composition samples have a volume of no more than about 20 ml.

14. The method of claim 1, wherein the lubricating oil composition samples have a volume of no more than about 15 ml.

15. The method of claim 1, wherein the lubricating oil composition samples have a volume of no more than about 10 ml.

16. The method of claim 1, further comprising the step of homogenizing the samples prior to measuring the dispersancy performance.

17. The method of claim 16, wherein the step of homogenizing the samples is performed by mechanical stirring.

18. The method of claim 16, wherein the step of homogenizing samples is performed by ultrasonic agitation.

19. The method of claim 1, further comprising the steps of compiling the dispersancy performance data sent to the microprocessor in an electronically stored database and constructing therefrom a combinatorial lubricating oil composition library.

20. The method of claim 1, wherein the at least one lubricating oil additive further comprises a diluent oil.

21. A method for screening lubricating oil composition samples for dispersancy performance, under program control, comprising:

(a) providing a plurality of different lubricating oil composition samples, each sample comprising: (i) a major amount of at least one base oil of lubricating viscosity, (ii) a minor amount of at least one lubricating oil additive, and (iii) a predetermined amount of a base oil-insoluble material selected from the group consisting of natural soot, synthetic soot, varnish-forming material, water and mixtures thereof;

(b) measuring the dispersancy performance of each test sample to provide corresponding dispersancy performance data results; and (c) automatically outputting the results of step (b);

wherein the step of measuring the dispersancy performance of each sample comprises dividing the sample into first and second portions, adding a predetermined amount of water to the second portion, applying to respective pieces of a chromatographic material at least three spots of each of the first and second portions of sample, heating selected spots to a predetermined temperature for a predetermined period of time, permitting the spots to elute into concentric rings, measuring an outer diameter of each ring and an inner diameter of each ring, calculating a ratio of inner diameter to outer diameter for the rings and calculating dispersancy performance data based upon the ratios for the rings.

22. A system for screening lubricant performance, under program control, comprising:

a) a plurality of test receptacles, each receptacle containing a different lubricating oil composition sample comprising: (i) a major amount of at least one base oil of lubricating viscosity, (ii) a minor amount of at least one lubricating oil additive, and (iii) a predetermined amount of a base oil-insoluble material selected from the group consisting of natural soot, synthetic soot, varnish-forming material, water and mixtures thereof;

b) receptacle moving means for individually positioning the test receptacles in a testing station for measurement of dispersancy performance of the respective sample; and c) means for measuring the dispersancy performance of the sample in the testing station to obtain dispersancy performance data associated with the sample and for transferring the dispersancy performance data to a computer controller.

23. The system of claim 22, wherein the receptacle moving means comprises a movable carriage.

24. The system of claim 22, wherein the receptacle moving means comprises a robotic assembly having a movable arm for grasping and moving a selected individual receptacle.

25. The system of claim 22, wherein the receptacle moving means comprises means for agitating the test receptacles.

26. The system of claim 22, wherein each test receptacle has a bar code affixed to an outer surface thereof.

27. The system of claim 26, further comprising a bar code reader.

28. The system of claim 22, wherein the base oil of lubricating viscosity is a natural or synthetic oil.

29. The system of claim 22, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents, and mixtures thereof.

30. The system of claim 22, wherein the at least one lubricating oil additive is an ashless dispersant.

31. The system of claim 22, wherein the means for measuring the dispersancy performance of the sample in the testing station comprises measuring the kinematic viscosity of each sample at a predetermined temperature to obtain dispersancy performance data associated with the sample and for transferring the dispersancy performance data to a computer controller.

32. The system of claim 22, wherein the means for measuring the dispersancy performance of the sample in the testing station comprises applying to a respective piece of a chromatographic material at least one spot of each sample, permitting the spot to elute into concentric rings, measuring an outer diameter of each ring and an inner diameter of each ring, calculating a ratio of inner diameter to outer diameter for the rings and calculating dispersancy performance data based upon the ratios for the rings.

33. The system of claim 22, wherein the means for measuring the dispersancy performance of the sample in the testing station comprises dividing the sample into first and second portions, adding a predetermined amount of water to the second portion, applying to respective pieces of a chromatographic material at least three spots of each of the first and second portions of sample, heating selected spots to a predetermined temperature for a predetermined period of time, permitting the spots to elute into concentric rings, measuring an outer diameter of each ring and an inner diameter of each ring, calculating a ratio of inner diameter to outer diameter for the rings and calculating dispersancy performance data based upon the ratios for the rings.

* * * * *